US010973690B2

(12) United States Patent
Liu

(10) Patent No.: US 10,973,690 B2
(45) Date of Patent: Apr. 13, 2021

(54) GOGGLE DEVICE AND SPECTACLE FRAME THEREOF

(71) Applicant: ASWAN INTERNATIONAL CORP., Taipei (TW)

(72) Inventor: Wei-Ting Liu, Taipei (TW)

(73) Assignee: ASWAN INTERNATIONAL CORP., Taipei (TW)

( * ) Notice: Subject to any disclaimer, the term of this patent is extended or adjusted under 35 U.S.C. 154(b) by 303 days.

(21) Appl. No.: 16/132,583

(22) Filed: Sep. 17, 2018

(65) Prior Publication Data

US 2020/0085624 A1   Mar. 19, 2020

(51) Int. Cl.
*A61F 9/02* (2006.01)

(52) U.S. Cl.
CPC ............. *A61F 9/027* (2013.01); *A61F 9/022* (2013.01); *A61F 9/025* (2013.01); *A61F 9/026* (2013.01); *A61F 2009/021* (2013.01)

(58) Field of Classification Search
CPC ...... A61F 9/027; A61F 9/02; B63C 2011/128; A44B 11/2553
USPC ..................................................... 2/448, 452
See application file for complete search history.

(56) References Cited

U.S. PATENT DOCUMENTS

| 4,607,398 | A | * | 8/1986 | Faulconer | ............... | A44B 11/14 2/452 |
| 2005/0045176 | A1 | * | 3/2005 | Godoy | ..................... | B63C 11/12 128/201.27 |
| 2005/0132478 | A1 | * | 6/2005 | Canavan | .................. | A61F 9/027 2/448 |
| 2009/0300888 | A1 | * | 12/2009 | Shiue | ...................... | A61F 9/027 24/193 |
| 2010/0229292 | A1 | * | 9/2010 | Tan | ......................... | A61F 9/025 2/452 |
| 2013/0139288 | A1 | * | 6/2013 | Gisquiere | .............. | A42B 3/185 2/10 |

* cited by examiner

*Primary Examiner* — Sally Haden
(74) *Attorney, Agent, or Firm* — Li & Cai Intellectual Property (USA) Office

(57) ABSTRACT

The present disclosure discloses a goggle device and a spectacle frame thereof. The spectacle frame includes a buckling structure arranged on an end portion thereof. The buckling structure has an accommodating space and an entrance in spatial communication with the accommodating space. The buckling structure includes a cantilever arranged in the accommodating space and a retaining wall that is arranged in the accommodating space and is spaced apart from the cantilever. A free end portion of the cantilever is arranged adjacent to the entrance, and the cantilever is rotatable between a lock position and an unlock position. When the cantilever is at the lock position, the free end portion shields the entrance. When the cantilever is rotated to the unlock position by an external force, the free end portion does not shield the entrance, and the cantilever is deformed to store an elastic force.

8 Claims, 12 Drawing Sheets

GOGGLE DEVICE AND SPECTACLE FRAME THEREOF

FIELD OF THE DISCLOSURE

The present disclosure relates to a goggle, and more particularly to a goggle device and a spectacle frame thereof.

BACKGROUND OF THE DISCLOSURE

A conventional goggle includes a spectacle frame and a belt fastened to the spectacle frame. Two opposite ends of the belt are inseparably fixed at two opposite portions of the spectacle frame, respectively. Based on the above, since the belt cannot be changed from the spectacle frame in the structure of the conventional goggle, the appearance of the belt is determined after the conventional goggle is produced. Accordingly, if a user wants to have various appearances of goggle, the user needs to buy a plurality of goggles.

SUMMARY OF THE DISCLOSURE

In response to the above-referenced technical inadequacies, the present disclosure provides a goggle device and a spectacle frame thereof to effectively improve the issues associated with conventional goggles.

In one aspect, the present disclosure provides a goggle device, which includes a spectacle frame, a light-permeable lens fastened to the spectacle frame, and a detachable belt. The spectacle frame includes two buckling structures respectively arranged on two opposite end portions thereof. Each of the two buckling structures has an accommodating space and an entrance in spatial communication with the accommodating space. Each of the two buckling structures includes a cantilever and a retaining wall. The cantilever is at least partially arranged in the accommodating space. A free end portion of the cantilever is arranged adjacent to the entrance, and the cantilever is rotatable between a lock position and an unlock position. The retaining wall is arranged in the accommodating space and spaced apart from the cantilever. The detachable belt detachably assembled with the two buckling structures, and the detachable belt includes an elongated belt body and two inserting members respectively fixed on two opposite ends of the belt body. Each of the two inserting members has a longitudinal direction that is substantially perpendicular to a longitudinal direction of the belt body, and the two inserting members are respectively inserted into the two buckling structures. In each of the two buckling structures and the corresponding inserting member, when the cantilever is rotated to the unlock position by an external force, the cantilever is deformed to store an elastic force, the inserting member is configured to insert into the accommodating space along the retaining wall through the entrance, and the cantilever and the retaining wall respectively abut against two opposite side portions of the inserting member. When the external force is removed, the cantilever is rotated to the lock position by releasing the elastic force, and the free end portion of the cantilever shields the entrance, so that movement of the inserting member in the accommodating space is restricted by the retaining wall and the cantilever, and the inserting member is retained in the buckling structure.

In one aspect, the present disclosure provides a spectacle frame of a goggle device, which includes a buckling structure arranged on an end portion thereof. The buckling structure has an accommodating space and an entrance in spatial communication with the accommodating space. The buckling structure includes a cantilever and a retaining wall. The cantilever is at least partially arranged in the accommodating space. A free end portion of the cantilever is arranged adjacent to the entrance, and the cantilever is rotatable between a lock position and an unlock position. The retaining wall is arranged in the accommodating space and spaced apart from the cantilever. When the cantilever is at the lock position, the free end portion of the cantilever shields the entrance; and when the cantilever is rotated to the unlock position by an external force, the free end portion of the cantilever does not shield the entrance, and the cantilever is deformed to store an elastic force.

Therefore, the spectacle frame and the goggle device in the present disclosure each can be formed with the buckling structure, and the cantilever of the buckling structure can be rotated to open or close the entrance, so as to be capable of being rapidly assembled with the inserting member of the detachable belt. Accordingly, the detachable belts on the spectacle frame of the goggle device in the present disclosure can be changed according to different requirements, so that the goggle device can have various appearances.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the detailed description and the accompanying drawings, in which.

DETAILED DESCRIPTION OF THE EXEMPLARY EMBODIMENTS

Figure 1:
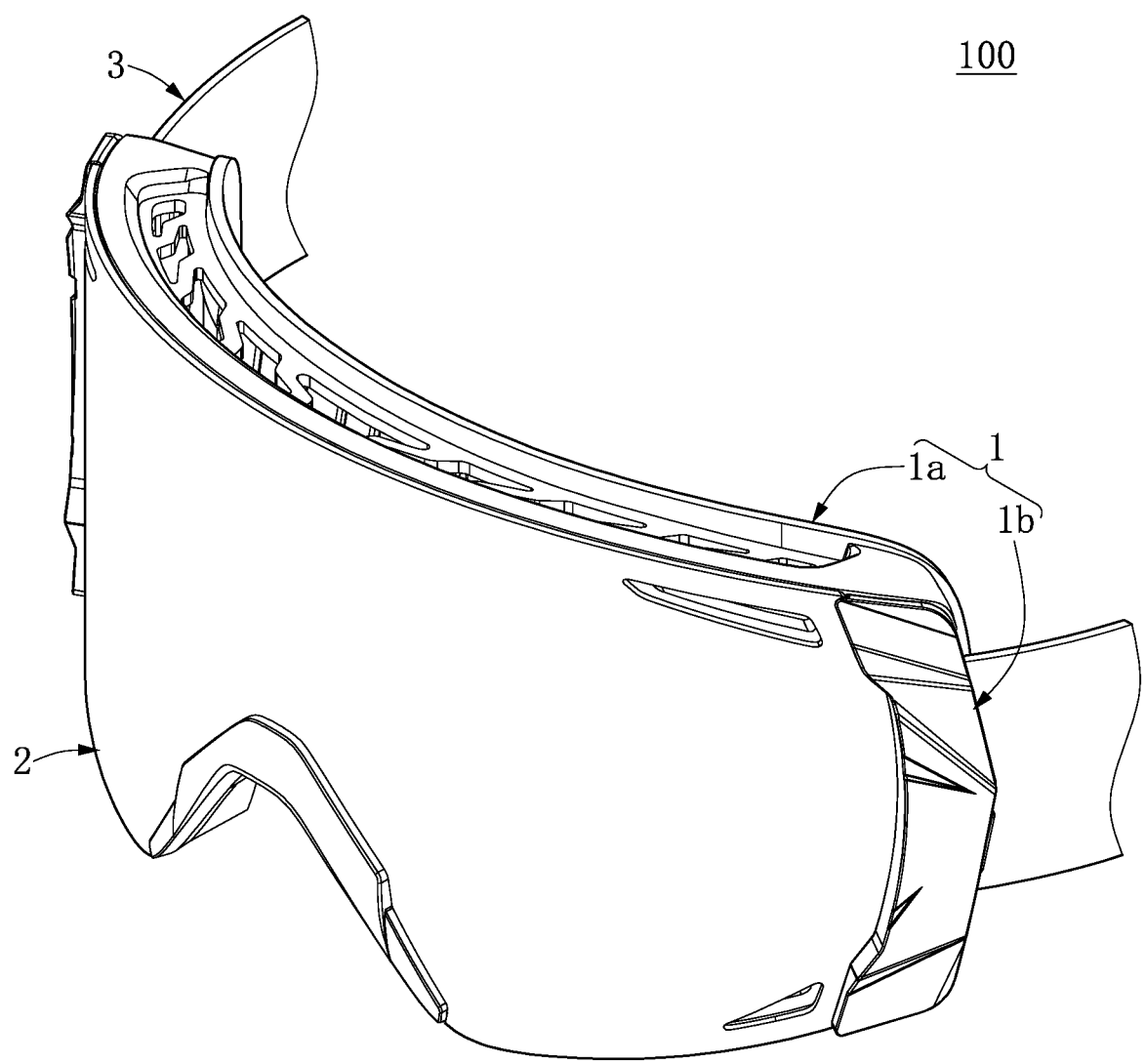
FIG. 1 is a perspective view of a goggle device according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1 to FIG. 12, an embodiment of the present disclosure provides a goggle device 100 for being worn on (e.g., being gaplessly attached to) a user's face so as to protect the user's eyes. The goggle device 100 in the present embodiment is preferably a snow goggle device that can be applied to a snow environment, but the present disclosure is not limited thereto.

Figure 2:
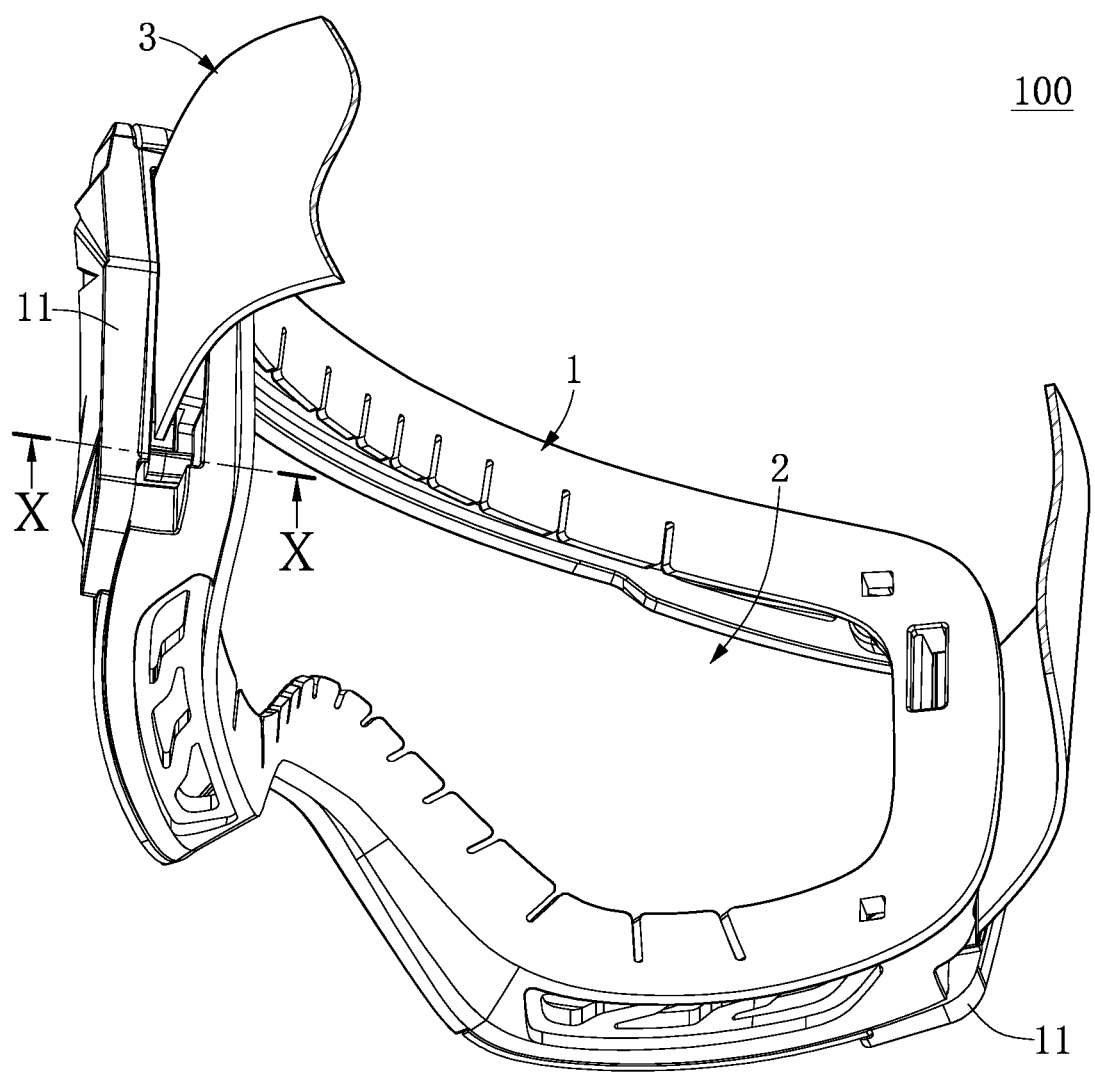
FIG. 2 is a perspective view of the goggle device from another angle of view.
Figure 3:
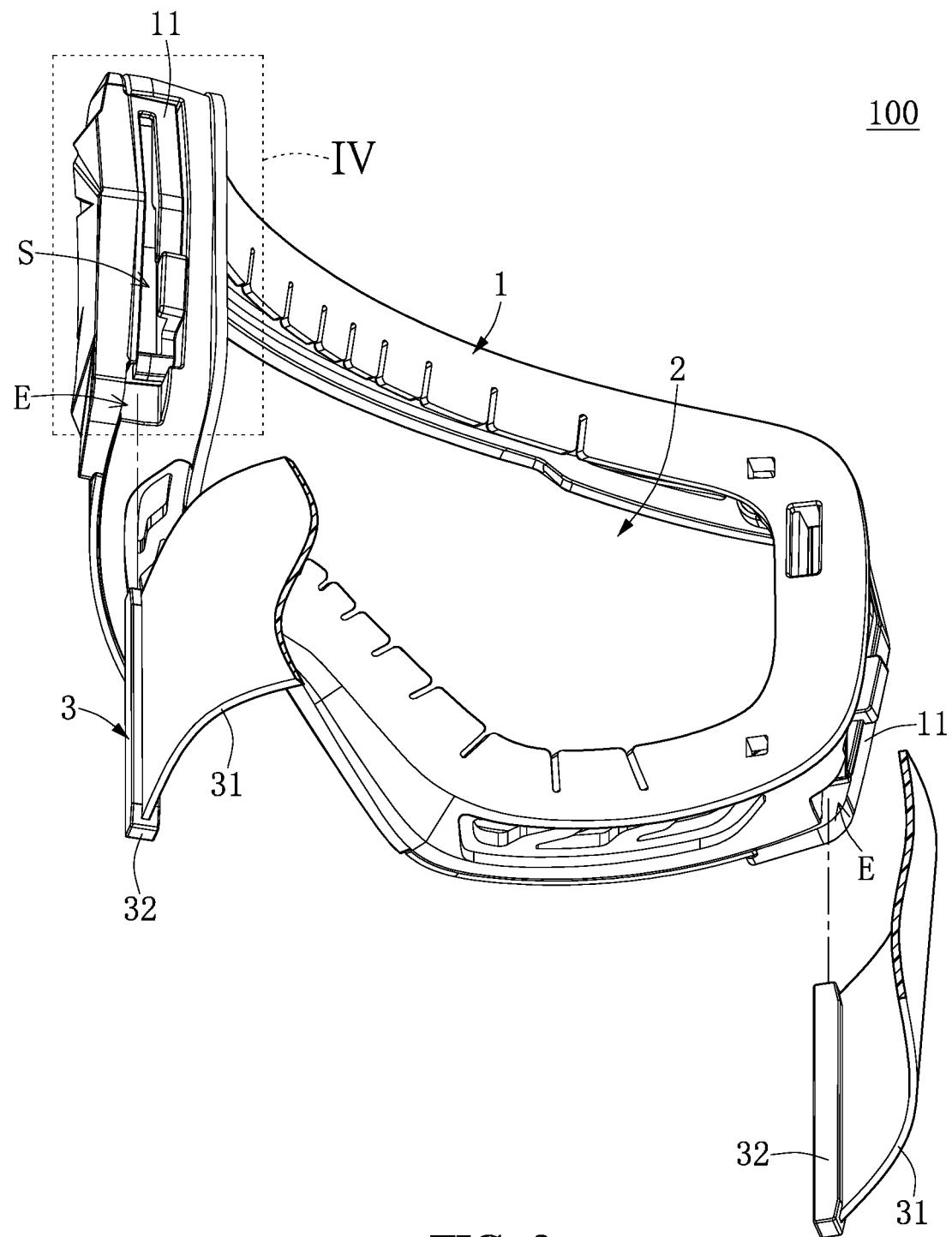
FIG. 3 is an exploded view of FIG. 2.

As shown in FIG. 1 to FIG. 3, the goggle device 100 includes a spectacle frame 1, a light-permeable lens 2 fastened to the spectacle frame 1, and a detachable belt 3 detachably assembled with the spectacle frame 1. The goggle device 100 in the present embodiment is provided with the spectacle frame 1 to be cooperated with the light-permeable lens 2 and the detachable belt 3, but the present disclosure is not limited thereto. For example, in other embodiments of the present disclosure, the spectacle frame 1 of the goggle device 100 can be independently sold, or can be cooperated with other components (e.g., the light-permeable lens 2 and two temples). The following description discloses the structure and connection relationship of each component of the goggle device 100.

Figure 4:
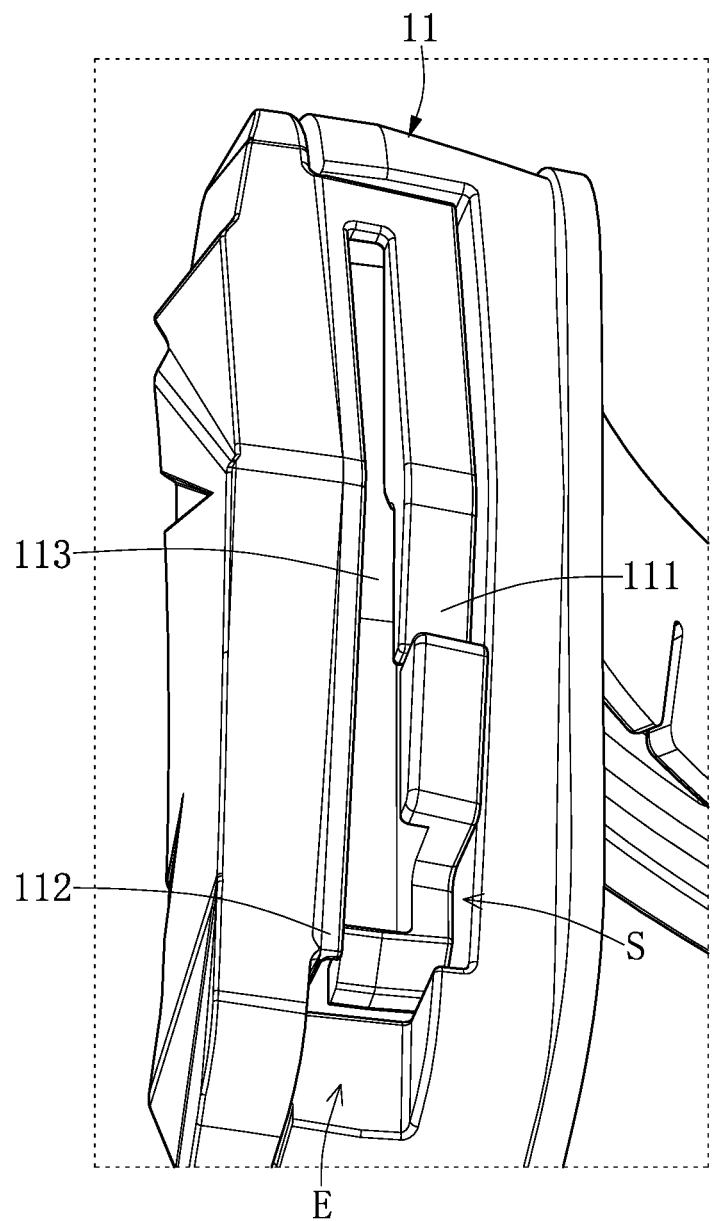
FIG. 4 is an enlarged view of portion IV of FIG. 3.

As shown in FIG. 3 and FIG. 4, the spectacle frame 1 includes two buckling structures 11 respectively arranged on two opposite end portions thereof, and the detachable belt 3 is detachably assembled with the two buckling structures 11. Each of the two buckling structures 11 has an accommodating space S and an entrance E in spatial communication with the accommodating space S. Moreover, the detachable belt 3 includes an elongated and flexible belt body 31 and two inserting members 32 respectively fixed on two opposite ends of the belt body 31. Each of the two inserting members 32 has a longitudinal direction that is substantially perpendicular to a longitudinal direction of the belt body 31, and the two inserting members 32 of the detachable belt 3 are respectively inserted into the two buckling structures 11 of the spectacle frame 1.

It should be noted that as the two buckling structures 11 are of the same or symmetrical structure, the following description discloses the structure of one of the two buckling structures 11 and the corresponding inserting member 32 for the sake of brevity, but the present disclosure is not limited thereto. For example, in other embodiments of the present disclosure, the spectacle frame 1 of the goggle device 100 can be formed with only one buckling structure 11 arranged on an end portion thereof, and the other end portion of the spectacle frame 1 is different from the buckling structure 11.

The buckling structure 11 includes a cantilever 111, a retaining wall 112, and a bottom wall 113. The retaining wall 112, the bottom wall 113, and at least part of the cantilever 111 are arranged in the accommodating space S. The cantilever 111, the retaining wall 112, and the bottom wall 113 of the buckling structure 11 are jointly formed to buckle the corresponding inserting member 32 of the detachable belt 3.

Figure 5:
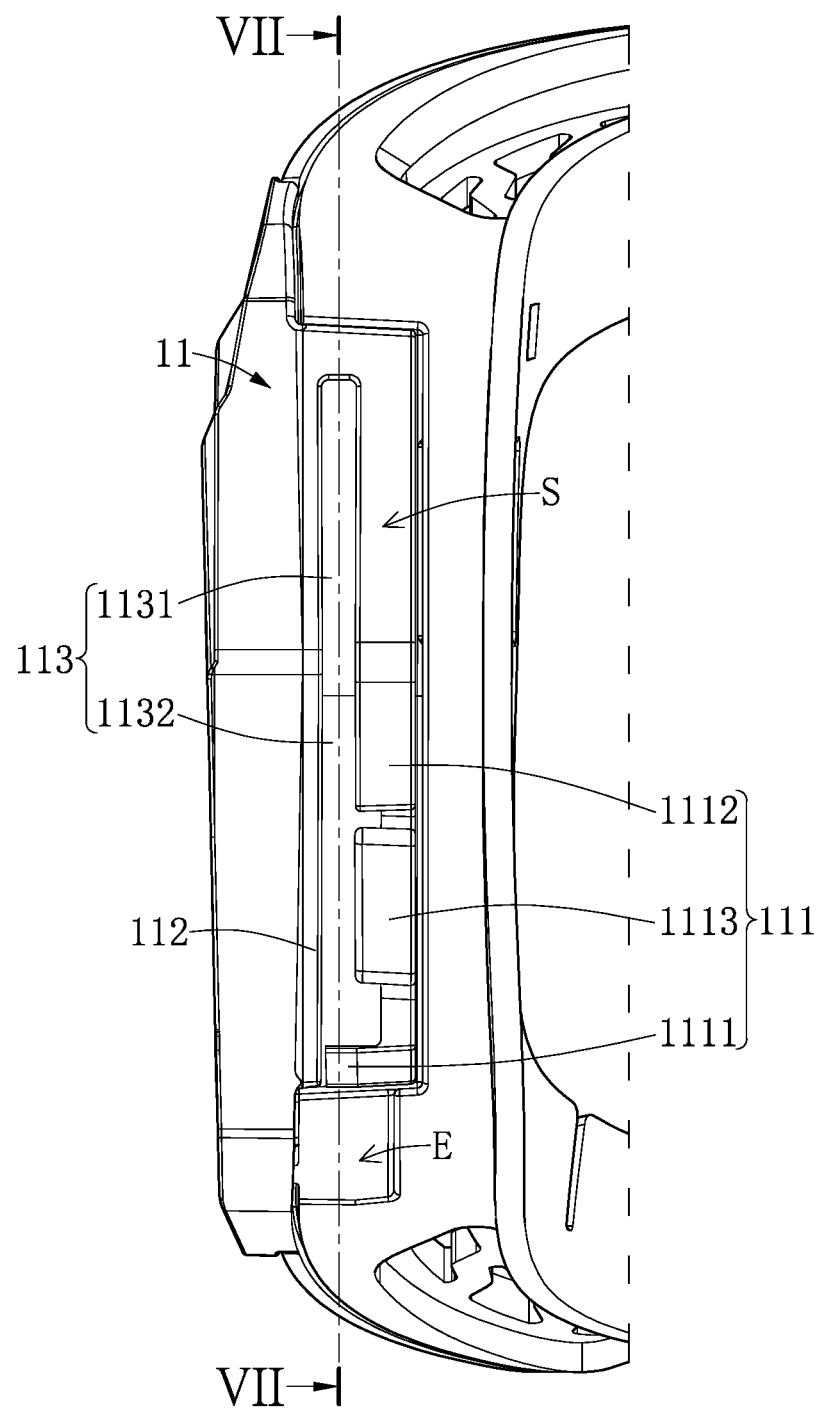
FIG. 5 is a side view of a buckling structure of the goggle device according to the present disclosure.
Figure 6:
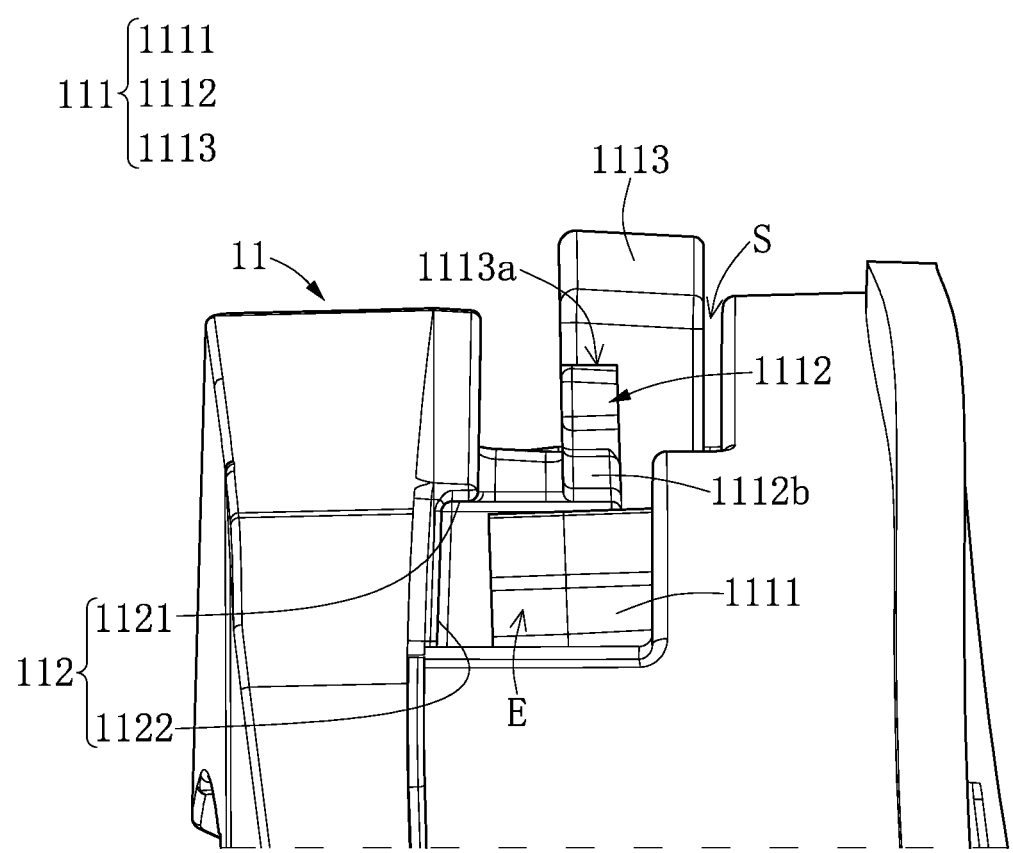
FIG. 6 is a bottom view of the buckling structure of the goggle device according to the present disclosure.
Figure 7:
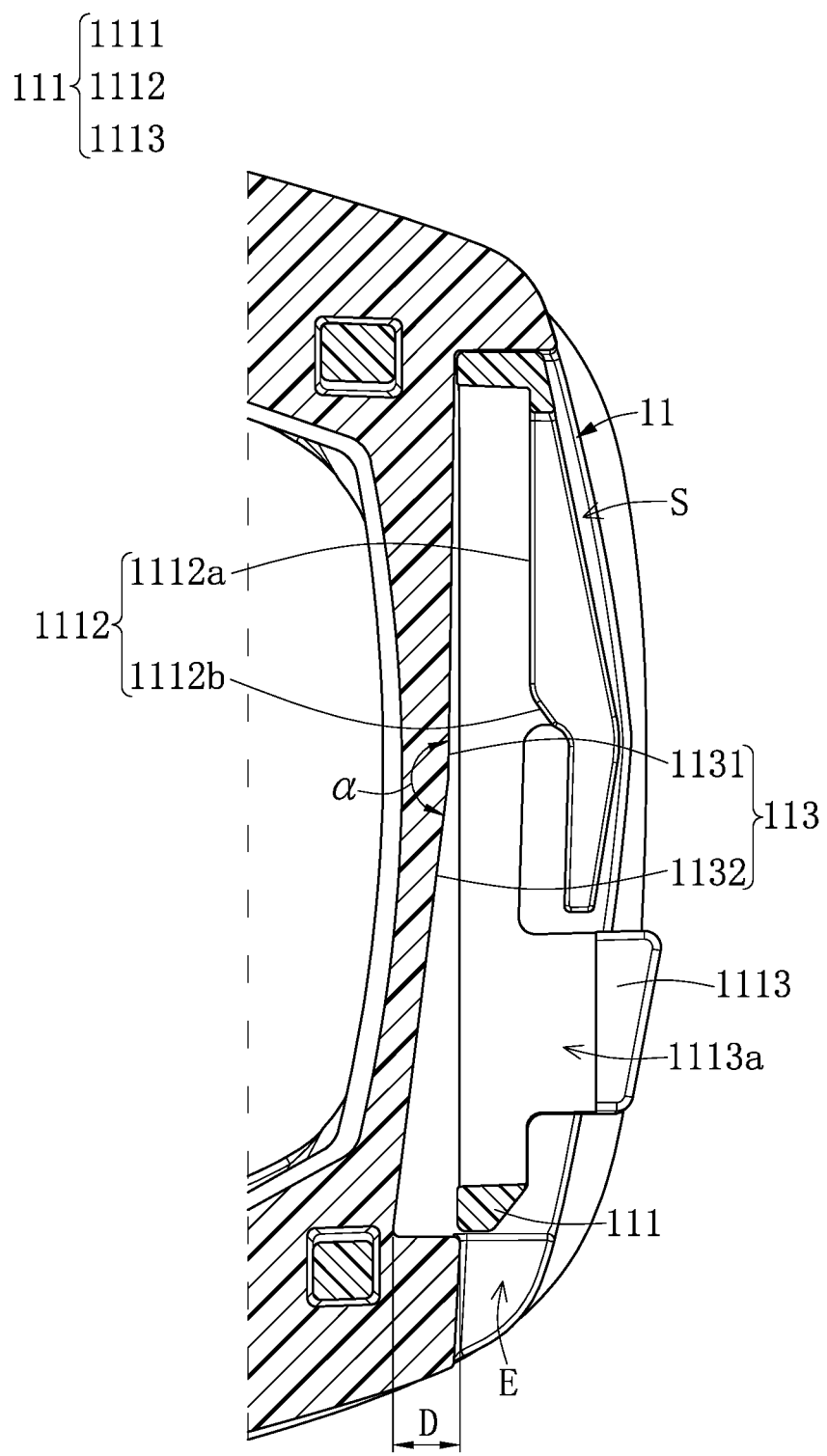
FIG. 7 is a cross-sectional view taken along line V II-V II of FIG. 5.

As shown in FIG. 5 to FIG. 7, the cantilever 111 includes a free end portion 1111, a guiding portion 1112, and a manipulation portion 1113 that is substantially arranged between the free end portion 1111 and the guiding portion 1112. The cantilever 111 is spaced apart from the retaining wall 112 and the bottom wall 113. A distance between the free end portion 1111 of the cantilever 111 and the retaining wall 112 is smaller than a distance between the guiding portion 1112 and the retaining wall 112, and is smaller than a distance between the manipulation portion 1113 and the retaining wall 112. An end of the cantilever 111 (e.g., a top end of the cantilever 111 shown in FIG. 7) opposite to the free end portion 1111 cannot move relative to the retaining wall 112, and is defined as a fixed end. The free end portion 1111 of the cantilever 111 is arranged adjacent to the entrance E.

Figure 8:
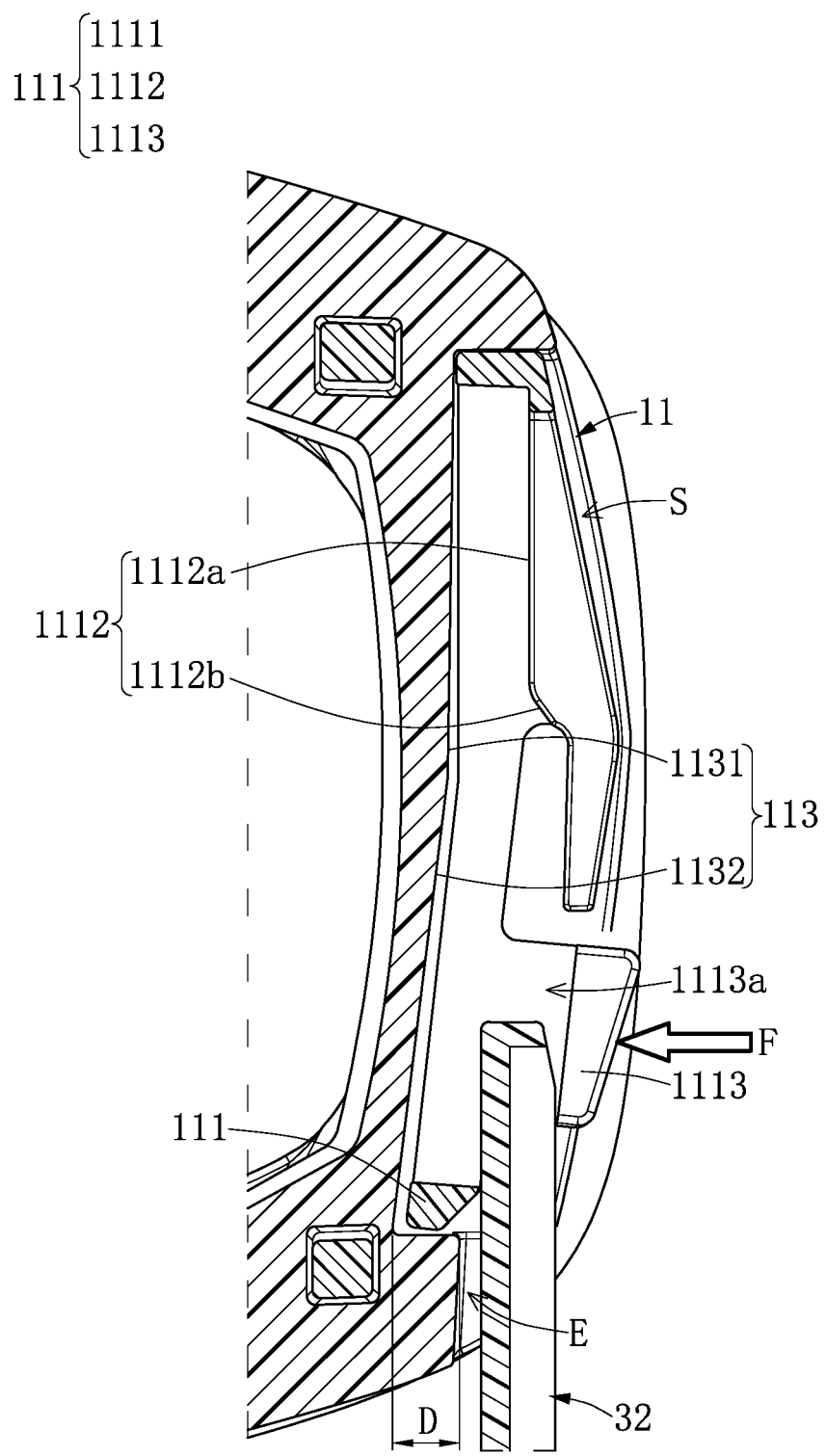
FIG. 8 is a cross-sectional view showing the buckling structure that is assembled with an inserting member.
Figure 9:
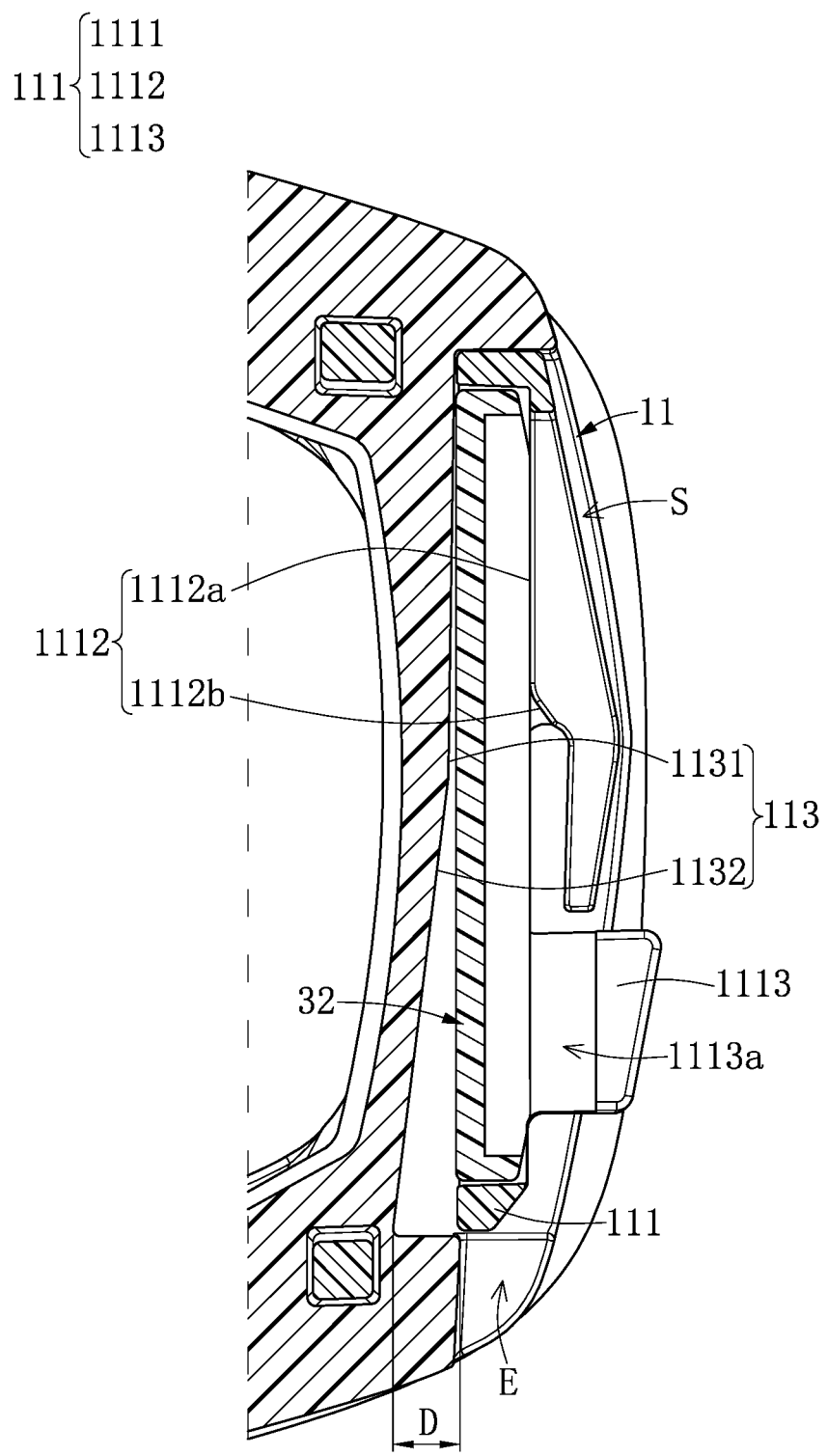
FIG. 9 is a cross-sectional view showing the buckling structure and the inserting member.

Specifically, the cantilever 111 is rotatable between a lock position (as shown in FIG. 7 to FIG. 9) and an unlock position (as shown in FIG. 8) by taking the fixed end to be a fulcrum. When the cantilever 111 is at the lock position (i.e., an original position), the free end portion 1111 of the cantilever 111 shields the entrance E. The term "shield" in the present embodiment means that the free end portion 1111 is arranged inside the entrance E, and at least part of the entrance E is blocked by the free end portion 1111 of the cantilever 111, but the present disclosure is not limited thereto. For example, in other embodiment of the present disclosure, the free end portion 1111 can be arranged outside the entrance E, or can be arranged in a region surroundingly defined by the entrance E.

In addition, when the cantilever 111 is rotated to the unlock position (as shown in FIG. 8) by receiving an external force F, the free end portion 1111 does not shield the entrance E, and the cantilever 111 is deformed to store an elastic force, so that the cantilever 111 can be rotated to the lock position by releasing the elastic force. In the present embodiment, the manipulation portion 1113 of the cantilever 111 protrudes out of the accommodating space S for providing press by the external force F (e.g., force from a user's finger), and a rotation of the cantilever 111 from the lock position to the unlock position in the present embodiment is defined by rotating the cantilever 111 toward the bottom wall 113 (or is a left rotation shown in FIG. 8), but the present disclosure is not limited thereto.

For example, in other embodiments of the present disclosure, the manipulation portion 1113 of the cantilever 111 can be arranged in the accommodating space S; or the external force F received by the cantilever 111 can be a pulling force, so that a rotation of the cantilever 111 from the lock position to the unlock position can be defined by rotating the cantilever 111 away from the bottom wall 113; or the buckling structure 11 can be added with an elastic member (e.g., a compression spring) arranged between the free end portion 1111 of the cantilever 111 and the bottom wall 113, so that the elastic member can further provide a force to the cantilever 111.

Specifically, as shown in FIG. 7 and FIG. 8, since the rotation of the cantilever 111 from the lock position to the unlock position in the present embodiment is defined by rotating the cantilever 111 toward the bottom wall 113, the buckling structure 11 is preferably formed with certain structures in cooperation with the rotation of the cantilever 111, which is disclosed as follows, but the present disclosure is not limited thereto.

As shown in FIG. 5 to FIG. 7, the bottom wall 113 includes a first segment 1131 and a second segment 1132 obliquely connected to the first segment 1131. The first segment 1131 and the second segment 1132 have an angle α there-between that is within a range of 150-170 degrees. When the cantilever 111 is at the lock position, the cantilever 111 is preferably spaced apart from the first segment 1131 and the second segment 1132 of the bottom wall 113. Moreover, the first segment 1131 is arranged on a portion of the bottom wall 113 (e.g., an upper portion of the bottom wall 113 shown in FIG. 7) away from the entrance E, the second segment 1132 is arranged on a portion of the bottom wall 113 (e.g., a lower portion of bottom wall 113 shown in FIG. 7) adjacent to the entrance E, and the second segment 1132 is spaced apart from the entrance E by a gap D.

As shown in FIG. 7 and FIG. 8, when the cantilever 111 is rotated toward the unlock position, the free end portion 1111 is moved toward the second segment 1132 until the free end portion 1111 is substantially located in the gap D. The manipulation portion 1113 of the cantilever 111 in the present embodiment has a notch 1113a recessed in an inner side thereof. A height of the notch 1113a with respect to the first segment 1131 is higher than a height of the free end portion 1111 with respect to the first segment 1131, so that when the cantilever 111 is at the unlock position and the free end portion 1111 is located in the gap D, the notch 1113a of the manipulation portion 1113 corresponds in position to (or is aligned with) the entrance E, thereby preventing the manipulation portion 1113 from shielding the entrance E.

As shown in FIG. 5 to FIG. 7, the guiding portion 1112 has a limiting surface 1112a facing the first segment 1131 and a guiding surface 1112b obliquely connected to the limiting surface 1112a. Moreover, the retaining wall 112 has a retaining surface 1121 facing the bottom wall 113 (e.g., the first segment 1131 and the second segment 1132) and a lateral surface 1122 connecting the retaining surface 1121 and the bottom wall 113 (e.g., the first segment 1131 and the second segment 1132).

The limiting surface 1112a of the guiding portion 1112 is parallel to the retaining surface 1121 of the retaining wall 112, and is non-parallel to the first segment 1131 of the bottom wall 113. A distance between the guiding portion 1112 and the lateral surface 1122 of the retaining wall 112 and a distance between the limiting surface 1112a of the guiding portion 1112 and the first segment 1131 of the bottom wall 113 each can be adjusted according to design requirements (e.g., a width and a thickness of the inserting member 32 of the detachable belt 3), and the present disclosure is not limited thereto.

Moreover, the guiding surface 1112b is arranged above the first segment 1131 of the bottom wall 113, and a projecting region defined by projecting the guiding surface 1112b onto the bottom wall 113 along a normal direction of the guiding surface 1112b is located on a common boundary of the first segment 1131 and the second segment 1132. Accordingly, when the cantilever 111 is at the unlock position (as shown in FIG. 8), the projecting region defined by projecting the guiding surface 1112b onto the bottom wall 113 along the normal direction of the guiding surface 1112b is located in a part of the first segment 1131 adjacent to the second segment 1132, so that the corresponding inserting member 32 of the detachable belt 3 can be guided to the first segment 1131 of the bottom wall 113 by the guiding surface 1112b.

Figure 10:
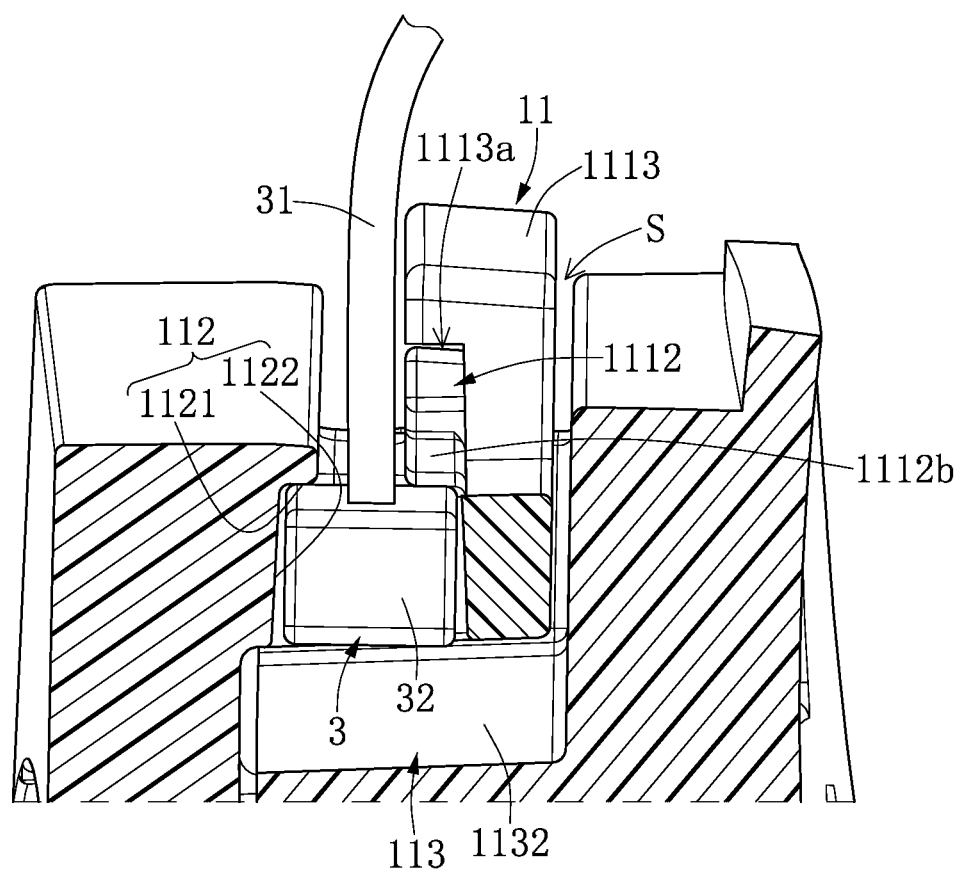
FIG. 10 is a cross-sectional view taken along line X-X of FIG. 2.

The buckling structure 11 of the present embodiment is disclosed in the above description, and the following description describes the relationship between each of the two buckling structures 11 and the corresponding inserting member 32. As shown in FIG. 7 to FIG. 10, when the manipulation portion 1113 of the cantilever 111 is rotated to the unlock position by the external force F, one side portion of the inserting member 32 (e.g., the left portion of the inserting member 32 as shown in FIG. 10) can be inserted into the accommodating space S along the retaining wall 112 (e.g., the retaining surface 1121 and the lateral surface 1122) by passing through the entrance E, and the other side portion of the inserting member 32 (e.g., the right portion of the inserting member 32 as shown in FIG. 10) can be inserted into the accommodating space S along the guiding surface 1112b by passing through the entrance E and the notch 1113a of the manipulation portion 1113, so that the cantilever 111 and the retaining wall 112 respectively abut against the two opposite side portions of the inserting member 32.

Specifically, the limiting surface 1112a of the cantilever 111 and the retaining surface 1121 of the retaining wall 112 respectively abut against the two opposite side portions of the inserting member 32. In other words, the inserting member 32 is substantially clamped between the first segment 1131 of the bottom wall 113, the limiting surface 1112a, and the retaining surface 1121.

When the external force F is removed (as shown in FIG. 9 and FIG. 10), the cantilever 111 is rotated to the lock position by releasing the elastic force of the cantilever 111, and the free end portion 1111 of the cantilever 111 shields the entrance E, so that movement of the inserting member 32 in the accommodating space S is restricted by the retaining wall 112 and the cantilever 111, and the inserting member 32 is retained in the buckling structure 11. In other words, the inserting member 32 is retained in a mechanism formed by the cantilever 111, the retaining wall 112, and the bottom wall 113 of the corresponding buckling structure 11.

Figure 11:
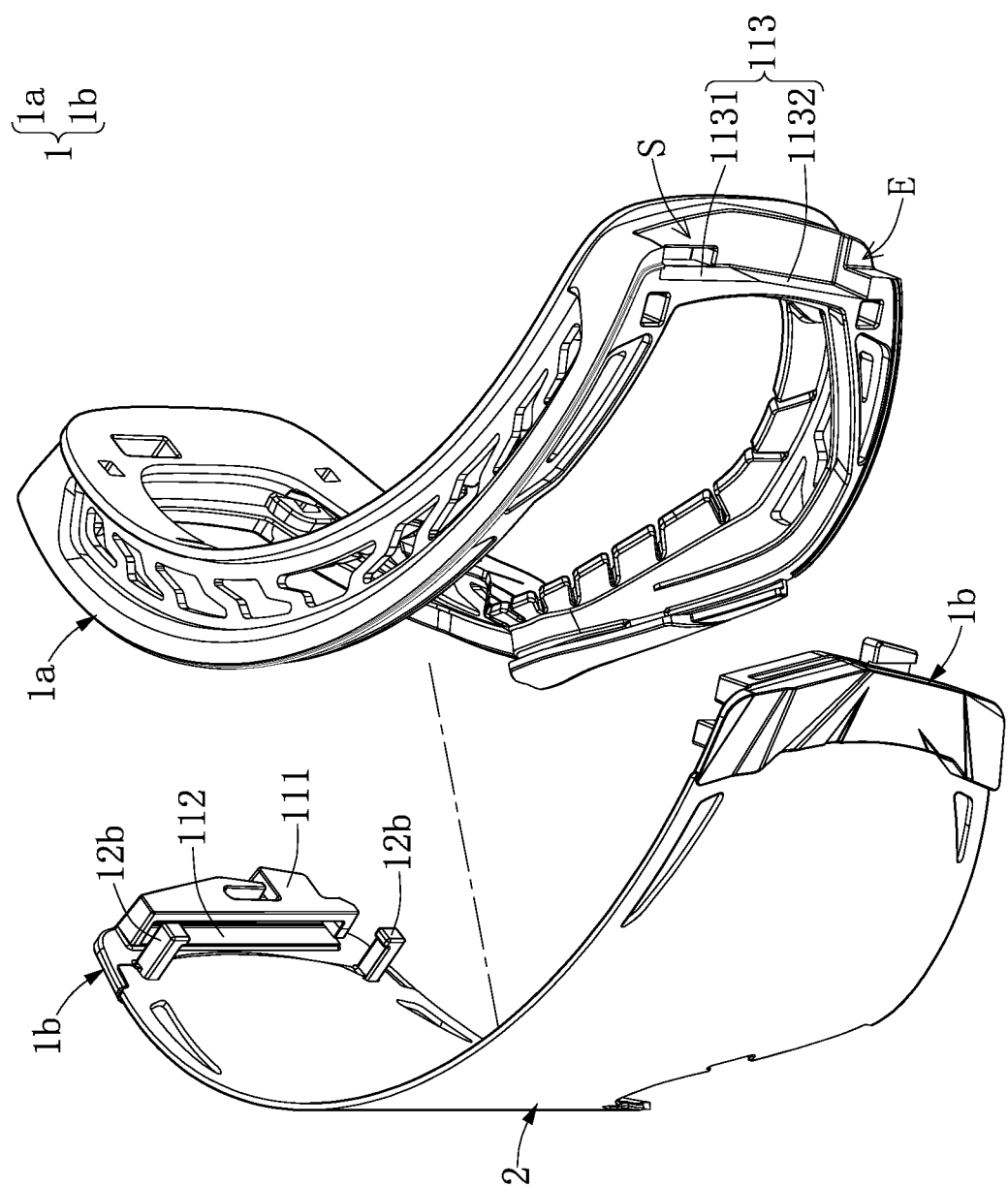
FIG. 11 is an exploded view of the goggle device when a detachable belt is omitted.
Figure 12:
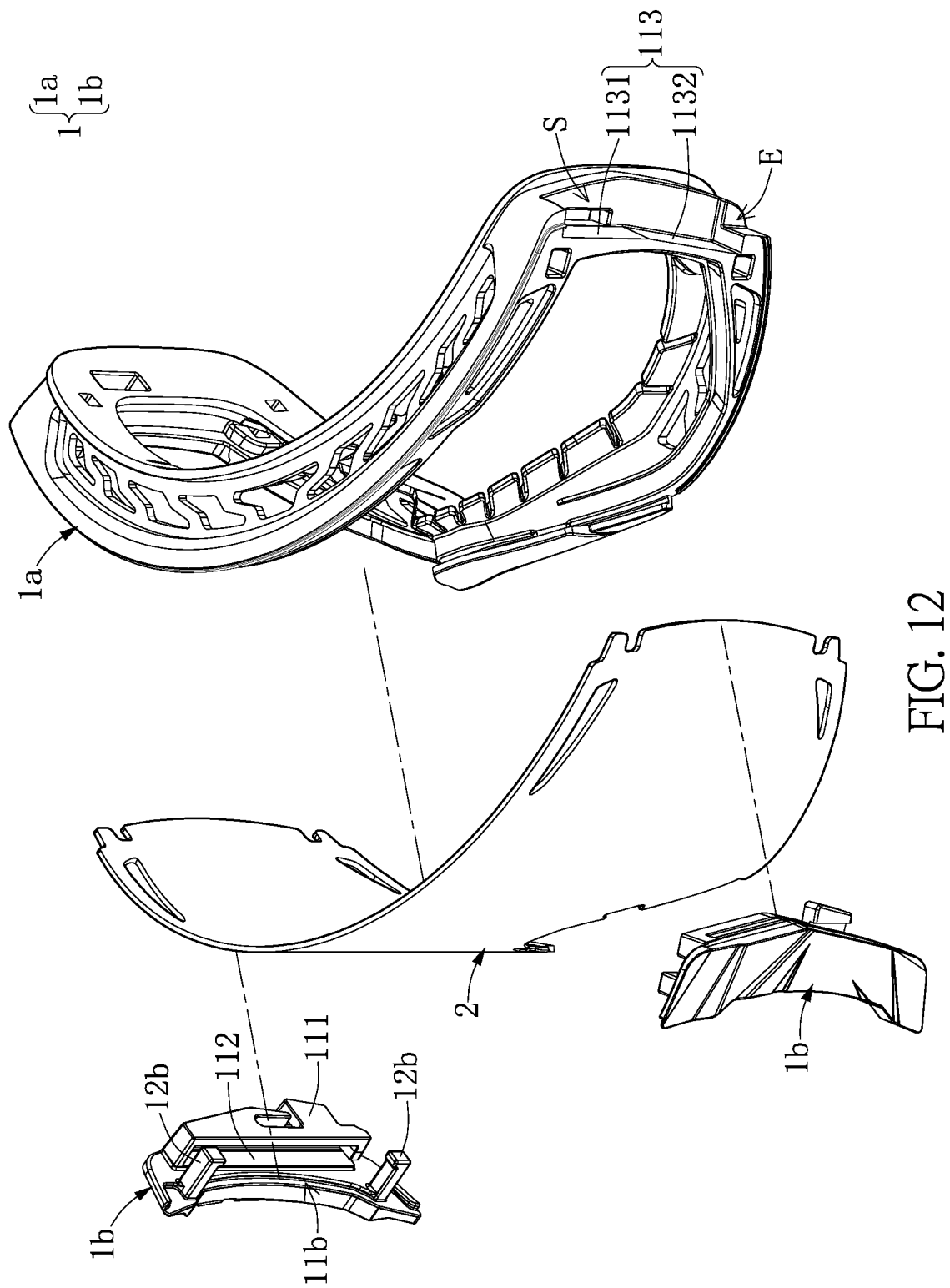
FIG. 12 is another exploded view of the goggle device when the detachable belt is omitted.

It should be noted that the buckling structure 11 in the above description is regarded as a single component, but the buckling structure 11 in the present embodiment is formed by assembling three components. As shown in FIG. 11 and FIG. 12, the spectacle frame 1 in the present embodiment includes a main frame 1a and two positioning members 1b fastened to the main frame 1a. The two positioning members 1b are cooperated with the main frame 1a so as to respectively define the two buckling structures 11, and two opposite portions of the light-permeable lens 2 are fastened to the main frame 1a through the two positioning members 1b, respectively, but the present disclosure is not limited thereto.

Specifically, a side portion of each of the two positioning members 1b (e.g., an outer portion of the positioning member 1b as shown in FIG. 12) is formed with the retaining wall 112 and the cantilever 111, and the other side portion of each of the two positioning members 1b (e.g., an inner portion of the positioning member 1b as shown in FIG. 12) has an edge groove 11b and two engaging posts 12b corresponding in position to the edge groove 11b. A portion of the cantilever 111 (e.g., the top of the manipulation portion 1113) of each of the two positioning members 1b protrudes from an outer periphery of the main frame 1a.

Moreover, the two engaging posts 12b of each of the two positioning members 1b are detachably inserted into the main frame 1a, so that the two opposite portions of the light-permeable lens 2 are respectively sandwiched between the two positioning members 1*b* and the main frame 1*a*. The two opposite portions of the light-permeable lens 2 are respectively received in the edge grooves 11*b* of the two positioning members 1*b*, and are respectively engaged with the engaging posts 12*b* of the two positioning members 1*b*.

In addition, the buckling structure 11 in the present embodiment is formed by assembling three components, but the present disclosure is not limited thereto. For example, in other embodiments of the present disclosure, the buckling structure 11 can be a single component or can be formed by assembling two or more than three components.

In conclusion, the spectacle frame 1 of the goggle device 100 in the present disclosure is formed with the buckling structure 11, and the cantilever 111 of the buckling structure 11 can be rotated to open or close the entrance E, so as to capable of being rapidly assembled with the inserting member 32 of the detachable belt 3. Accordingly, the detachable belts 3 on the spectacle frame 1 of the goggle device 100 in the present disclosure can be changed according to different requirements, so that the goggle device 100 can have various appearances.

Moreover, since the assembling of the inserting member 32 is implemented by pressing the buckling structure 11 (e.g., the rotation of the cantilever 111 from the lock position to the unlock position is defined by rotating the cantilever 111 toward the bottom wall 113) for providing a convenient operation to a user, the buckling structure 11 of the present disclosure can be formed with certain structures in cooperation with the rotation of the cantilever 111, such as: the angle α defined by the first segment 1131 and the second segment 1132 of the bottom wall 113, the gap D between the second segment 1132 and the entrance E, the guiding surface 1112*b* of the guiding portion 1112 corresponding in position to the common boundary of the first segment 1131 and the second segment 1132, and the manipulation portion 1113 of the cantilever 111 formed with the notch 1113*a*. It should be noted that the above features can be implemented to form the buckling structure 11 with a pressable structure, but the spectacle frame 1 is not limited to have all of the above features.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A goggle device, comprising:
   a spectacle frame including two buckling structures respectively arranged on two opposite end portions thereof, wherein each of the two buckling structures has an accommodating space and an entrance in spatial communication with the accommodating space, and each of the two buckling structures includes:
      a cantilever at least partially arranged in the accommodating space, wherein a free end portion of the cantilever is arranged adjacent to the entrance, and the cantilever is rotatable between a lock position and an unlock position; and
      a retaining wall arranged in the accommodating space and spaced apart from the cantilever;
   a light-permeable lens fastened to the spectacle frame; and
   a detachable belt detachably assembled with the two buckling structures, and the detachable belt including:
      an elongated belt body; and
      two inserting members respectively fixed on two opposite ends of the belt body, wherein each of the two inserting members has a longitudinal direction that is substantially perpendicular to a longitudinal direction of the belt body, and the two inserting members are respectively inserted into the two buckling structures;
   wherein in each of the two buckling structures and the corresponding inserting member, when the cantilever is rotated to the unlock position by an external force, the cantilever is deformed to store an elastic force, the inserting member is configured to insert into the accommodating space along the retaining wall through the entrance, and the cantilever and the retaining wall respectively abut against two opposite side portions of the inserting member; and when the external force is removed, the cantilever is rotated to the lock position by releasing the elastic force, and the free end portion of the cantilever shields the entrance, so that movement of the inserting member in the accommodating space is restricted by the retaining wall and the cantilever, and the inserting member is retained in the buckling structure,
   wherein each of the two buckling structures includes a bottom wall having a first segment and a second segment in each of the two buckling structures, the first segment is arranged on a portion of the bottom wall away from the entrance, the second segment is arranged on a portion of the bottom wall adjacent to the entrance, and the second segment is spaced apart from the entrance by a gap; and when the cantilever is rotated toward the unlock position, the free end portion is moved toward the second segment until the free end portion is substantially located in the gap,
   wherein in each of the two buckling structures, the cantilever includes a guiding portion, the guiding portion has a limiting surface facing the first segment and a guiding surface obliquely connected to the limiting surface, and the limiting surface and the retaining wall are parallel to each other and respectively abut against the two opposite side portions of the corresponding inserting member.

2. The goggle device according to claim 1, wherein in each of the two buckling structures, the first segment and the second segment have an angle there-between that is within a range of 150-170 degrees, and when the cantilever is at the lock position, the cantilever is spaced apart from the first segment and the second segment of the bottom wall.

3. The goggle device according to claim 1, wherein in each of the two buckling structures, the limiting surface is non-parallel to the first segment, and a projecting region defined by projecting the guiding surface onto the bottom wall along a normal direction of the guiding surface is located on a common boundary of the first segment and the second segment.

4. The goggle device according to claim 1, wherein in each of the two buckling structures, the cantilever has a manipulation portion arranged between the free end portion and the guiding portion, and the manipulation portion has a notch recessed in an inner side thereof; and in each of the two buckling structures and the corresponding inserting member, when the cantilever is at the unlock position, the inserting member is configured to insert into the accommodating space along the guiding surface by passing through the notch of the manipulation portion.

5. The goggle device according to claim 1, wherein the spectacle frame includes a main frame and two positioning members fastened to the main frame, the two positioning members are cooperated with the main frame so as to respectively define the two buckling structures, and two opposite portions of the light-permeable lens are fastened to the main frame through the two positioning members, respectively.

6. The goggle device according to claim 5, wherein a side portion of each of the two positioning members is formed with the retaining wall and the cantilever, and the other side portion of each of the two positioning members has an edge groove and two engaging posts corresponding in position to the edge groove; a portion of the cantilever of each of the two positioning members protrudes from an outer periphery of the main frame; the two engaging posts of each of the two positioning members are detachably inserted into the main frame, so that the two opposite portions of the light-permeable lens are respectively sandwiched between the two positioning members and the main frame;

and the two opposite portions of the light-permeable lens are respectively received in the edge grooves of the two positioning members, and are respectively engaged with the engaging posts of the two positioning members.

7. A spectacle frame of a goggle device, comprising: a buckling structure arranged on an end portion thereof, wherein the buckling structure has an accommodating space and an entrance in spatial communication with the accommodating space, and the buckling structure includes:
 a cantilever at least partially arranged in the accommodating space, wherein a free end portion of the cantilever is arranged adjacent to the entrance, and the cantilever is rotatable between a lock position and an unlock position; and
 a retaining wall arranged in the accommodating space and spaced apart from the cantilever;
 wherein when the cantilever is at the lock position, the free end portion of the cantilever shields the entrance; and when the cantilever is rotated to the unlock position by an external force, the free end portion of the cantilever does not shield the entrance, and the cantilever is deformed to store an elastic force,
 wherein the buckling structure includes a bottom wall having a first segment and a second segment, wherein the first segment is arranged on a portion of the bottom wall away from the entrance, the second segment is arranged on a portion of the bottom wall adjacent to the entrance, and the second segment is spaced apart from the entrance by a gap, and wherein when the cantilever is rotated toward the unlock position, the free end portion is moved toward the second segment until the free end portion is substantially located in the gap,
 wherein the cantilever includes a guiding portion, wherein the guiding portion has a limiting surface facing the first segment and a guiding surface obliquely connected to the limiting surface, and wherein the limiting surface and the retaining wall are parallel to each other and are configured to respectively abut against two opposite side portions of an inserting member.

8. The spectacle frame according to claim 7, wherein the spectacle frame includes a main frame and two positioning members fastened to the main frame, the buckling structure is formed on one of the two positioning members and a corresponding portion of the main frame, and two opposite portions of a light-permeable lens are configured to be fixed at the main frame through the two positioning members, respectively.

* * * * *